(12) United States Patent
Iizuka et al.

(10) Patent No.: US 9,117,009 B2
(45) Date of Patent: Aug. 25, 2015

(54) REPORT CREATION SUPPORT APPARATUS, CREATION SUPPORT METHOD THEREOF AND PROGRAM

(75) Inventors: Yoshio Iizuka, Yokohama (JP); Kiyohide Satoh, Kawasaki (JP); Masami Kawagishi, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/302,885

(22) Filed: Nov. 22, 2011

(65) Prior Publication Data

US 2012/0134555 A1    May 31, 2012

(30) Foreign Application Priority Data

Nov. 29, 2010   (JP) .................................. 2010-264922

(51) Int. Cl.
*G06K 9/00* (2006.01)
*G06F 19/00* (2011.01)

(52) U.S. Cl.
CPC .......... *G06F 19/321* (2013.01); *G06F 19/3487* (2013.01)

(58) Field of Classification Search
CPC ....... G06K 9/46; G06K 9/62; G06K 9/00214; G06K 9/00281; G06K 9/00288; G06K 9/4652; G06K 9/6261
See application file for complete search history.

(56) References Cited

U.S. PATENT DOCUMENTS

| | | | |
|---|---|---|---|
| 2005/0152592 A1* | 7/2005 | Kasai | 382/132 |
| 2005/0207645 A1* | 9/2005 | Nishimura et al. | 382/170 |
| 2008/0212856 A1* | 9/2008 | Oosawa et al. | 382/128 |
| 2008/0215630 A1* | 9/2008 | Oosawa et al. | 707/104.1 |

FOREIGN PATENT DOCUMENTS

| | | |
|---|---|---|
| JP | H11-238078 A | 8/1999 |
| JP | 2002-230518 A | 8/2002 |
| JP | 2007-305107 A | 11/2007 |
| JP | 2009-082443 A | 4/2009 |

* cited by examiner

*Primary Examiner* — Barry Drennan
*Assistant Examiner* — Amandeep Saini
(74) *Attorney, Agent, or Firm* — Canon USA Inc. IP Division

(57) ABSTRACT

In an apparatus configured to generate a report based on diagnosis target images, image characteristic conditions to identify a plurality of diagnosis target images specified by a user as a group are derived, search conditions of images similar to the diagnosis target images by using the obtained image characteristic conditions are determined, a database is searched for one or more similar images satisfying the search conditions; and image findings satisfying predetermined conditions is extracted from image findings attached to one or more obtained similar images.

19 Claims, 12 Drawing Sheets

FIG.5

510 IMAGE FINDINGS INPUT AREA

| SIZE (cm): | |
|---|---|
| OVERALL SHAPE: | ROUND ▼ |
| SPICULATION: | NOT RECOGNIZED ▼ |
| ILL-DEFINED BORDER: | MANY/STRONG ▼ |
| CALCIFICATION: | ▼ |
| CAVITATION: | ▼ |
| INVOLVEMENT: | ▼ |
| AIR BRONCHOGRAM: | ▼ |

REPORT CREATION SUPPORT APPARATUS, CREATION SUPPORT METHOD THEREOF AND PROGRAM

BACKGROUND OF THE INVENTION

1. Field of the Invention

The present invention relates to a technology to support creation of a report on medical images.

2. Description of the Related Art

Results of image diagnosis performed by observing medical images by a medical doctor are summarized as an image diagnosis report. In the past, image findings and impression of image diagnosis were written by hand in special writing paper by the medical doctor. In recent years, with implementation of electronic management of medical documents for the purpose of making medical services more efficient, image diagnosis reports are increasingly created electronically. However, many conventional report creation support apparatuses still let the medical doctor input image findings and impression of image diagnosis as free sentences and thus, it takes considerable time for the medical doctor to input free sentences and a significant burden is placed on the medical doctor to create a report.

Previous attempts to address the above problems have been made. Japanese Patent Application Laid-Open No. 2007-305107 proposes a report creation support technology that makes use of image search and report sentence templates. Specifically, a report creation support apparatus holds report sentence templates created based on reports about a plurality of case images (created beforehand). When a medical image (hereinafter referred to as a diagnosis target image) of a patient to be diagnosed is input, the report creation support apparatus performs a search of the past case images to determine if past case images similar to the diagnosis target image exist. Then, the report creation support apparatus acquires a report sentence template corresponding to one similar image acquired by the search and displays the template. Then, the medical doctor can reduce time and efforts to create report sentences by correcting the displayed template.

A conventional method for searching similar images is a method by which image characteristics of a plurality of case images accumulated in advance and image characteristics of an image to be diagnosed are compared and some similar images are selected in descending order of similarity between image characteristics. However, it is necessary to appropriately set items (hereinafter referred to as "search parameters"), for example, which image characteristics to compare, how to define the similarity between image characteristics, and the level of similarity (a value of threshold) above which an image is determined to be a similar image.

According to the conventional search method, there is the possibility that a similar image fitting for the user's choice may not be searched for if search parameters are not appropriately set. More specifically, almost no case image which the user finds to be similar may be searched or many case images found by the user not to be similar may be searched. Therefore, it is necessary for the user to set appropriate search parameters to search for a similar image fitting the user's choice.

In general, however, there are many types (several tens of types) of image characteristics and several definition methods of similarity and if the similarity is continuous, the threshold can infinitely be changed. Therefore, the work to search for search parameters providing a similar image fitting the user's choice by trial and error while viewing search results of similar images takes time and effort.

According to the conventional search method, as described above, there is a problem that a similar image fitting for the user's choice may not always be searched.

Further, according to the method discussed by Japanese Patent Application Laid-Open No. 2007-305107, even if a plurality of similar images is obtained by the search, only a report sentence template corresponding to one similar image can be used for report creation support of a diagnosis target image. In other words, there is a problem that information obtained from a plurality of reports corresponding to the plurality of similar images cannot be used simultaneously.

SUMMARY OF THE INVENTION

The present invention is directed to an electronic apparatus capable of efficiently performing a search of similar images fitting the user's choice and need. Further, information obtained from reports corresponding to similar images obtained from the search can be used simultaneously.

One aspect of the present invention is directed to an apparatus configured to generate a report based on diagnosis target images and includes a derivation unit that derives image characteristic conditions to identify a plurality of diagnosis target images specified by a user as a group, a determination unit that determines search conditions of images similar to the diagnosis target images by using the image characteristic conditions obtained by the derivation unit, a search unit that searches a database for one or more similar images satisfying the search conditions, and an extraction unit that extracts image findings satisfying predetermined conditions from image findings attached to one or more similar images obtained by the search unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

FIG. 5 is a schematic diagram illustrating the report creation screen example of the report creation support apparatus according to the first exemplary embodiment of the present invention.

FIG. 6-1 is a flow chart exemplifying a control procedure of the report creation support apparatus according to the first exemplary embodiment of the present invention.

FIG. 6-2 is a flow chart illustrating the first exemplary embodiment of the present invention and exemplifying a detailed control procedure of step S604 in FIG. 6-1.

DESCRIPTION OF THE EMBODIMENTS

Various exemplary embodiments, features, and aspects of the invention will be described in detail below with reference to the drawings.

However, the scope of the invention is not limited to illustrated examples.

Figure 1:
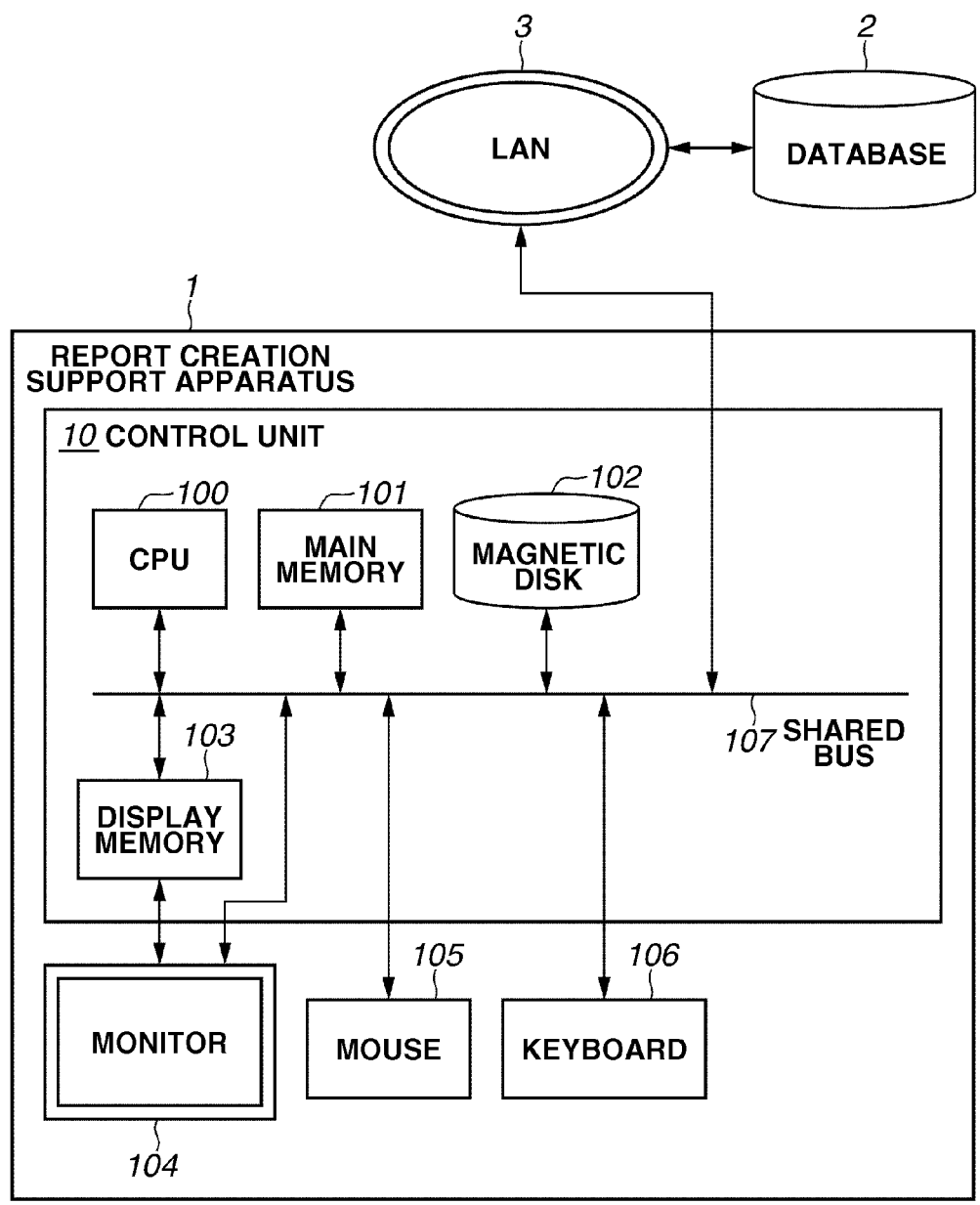
FIG. 1 is a schematic diagram exemplifying a system configuration of a report creation support system including a report creation support apparatus according to a first exemplary embodiment of the present invention.

FIG. 1 is a schematic diagram exemplifying a configuration of a report creation support system including a report creation support apparatus according to the first exemplary embodiment of the present invention.

The report creation support system illustrated in FIG. 1 includes a report creation support apparatus 1, a database 2, and a LAN (Local Area Network) 3.

The report creation support apparatus 1 includes a control unit 10, a monitor 104, a mouse 105, and a keyboard 106. The control unit 10 includes a central processing unit (CPU) 100, a main memory 101, a magnetic disk 102, a display memory 103, and a shared bus 107.

The CPU 100 executes programs stored in the main memory 101 so that the CPU 100 exercises various kinds of control such as communication with the database 2 and overall control of the report creation support apparatus 1. The CPU 100 mainly controls the operation of each element of the report creation support apparatus 1.

The main memory 101 stores a control program executed by the CPU 100 or provides a work area when a program is executed by the CPU 100.

The magnetic disk 102 stores various kinds of application software including an operating system (OS), device drives of peripheral devices, and a program for performing diagnostic support processing described below.

The display memory 103 temporarily stores display data for the monitor 104.

The monitor 104 is, for example, a CRT monitor or liquid crystal display (LCD) monitor and displays images or the like based on data from the display memory 103.

The monitor 104 displays display data stored in the display memory 103 based on the control of the CPU 100.

The mouse 105 is a pointing device that enables a user (medical doctor) to input, control and manipulate data. Characters and the like are input by the user with the keyboard 106. The above elements are mutually communicably connected by the shared bus 107.

In the present exemplary embodiment, the report creation support apparatus 1 can read medical image data, image characteristics, and image findings findings from the database 2 via the LAN 3. The medical image data, image characteristics, and image findings are stored in association with each other and the associated medical image data, image characteristics, and image findings findings can be read by using, for example, an identifier (image ID) of the medical image data as a search key.

Types of medical image data include simple X-ray images, X-ray CT images, MRI images, PET images, SPECT images, and ultrasonic images. Normally, medical image data is stored in the database 2 as a file conforming to the Digital Imaging and Communications in Medicine (DICOM) international standard concerning communication/storage of medical images.

The above apparatus configuration can be constructed by using general-purpose computers and peripheral devices thereof. A control procedure of a report creation support apparatus according to the present invention described below referring to FIGS. 6-1 and 6-2 can be realized as a program to be executed on the computer.

Figure 2:
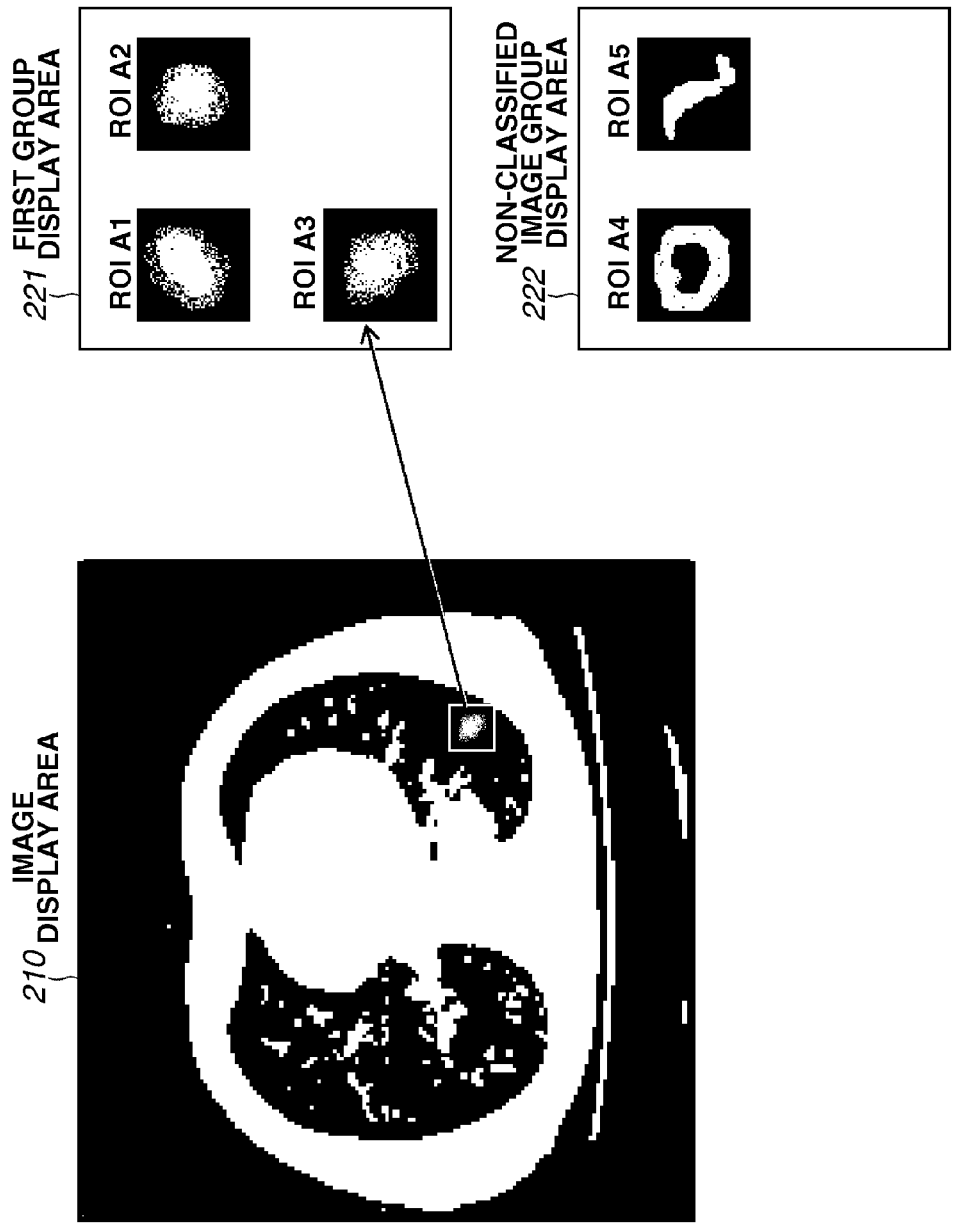
FIG. 2 is a diagram illustrating an image display screen example of the report creation support apparatus according to the first exemplary embodiment of the present invention.

FIG. 2 is a diagram illustrating an image display screen example of the report creation support apparatus according to the first exemplary embodiment of the present invention.

In FIG. 2, medical image data of a patient to be diagnosed is displayed in an image display area 210 inside the monitor 104. If the medical image data contains one image of a simple X-ray image or the like, the image is displayed in the image display area 210. On the other hand, if the medical image data contains a plurality of cross section images such as CT images or MRI images, one cross section image selected according to a user's instruction is displayed in the image display area 210.

The user can specify a region of interest (ROI) of the medical image displayed in the image display area 210 by using the mouse 105 or the keyboard 106 to issue an instruction. The image (ROI image) in the specified ROI is displayed in a non-classified image group display area 222 as a diagnosis target image. After the ROI is specified, the user classifies ROI images in the non-classified image group display area 222 into a group collecting similar images at the user's choice. This operation is performed by, for example, dragging & dropping the ROI image to be classified into the same group from the non-classified image group display area 222 into a first group display area 221 by the mouse 105. According to the example in FIG. 2, five ROIs (ROI A1 to A5) are specified and A1, A2, and A3 of the five ROIs are specified as the same group (first group).

In FIG. 2, the first group display area 221 collecting first similar images and the non-classified image group display area 222 collecting non-classified ROI images are illustrated. Though not illustrated in FIG. 2, the user can classify ROI images into n groups and a non-classified image group by further displaying n (n≥2) group display areas to collect second, third, ... similar images.

In the example in FIG. 2, only one cross section image is displayed in the image display area 210, but three orthogonal cross section images (not illustrated) may be displayed. By specifying the region of interest of the medical image on the three orthogonal cross section images, the region of interest (VOI) of a three-dimensional medical image can be specified. In this case, an ROI image described below is replaced by a VOI image and image characteristics of the ROI image is replaced by image characteristics of the VOI image.

Figure 3:
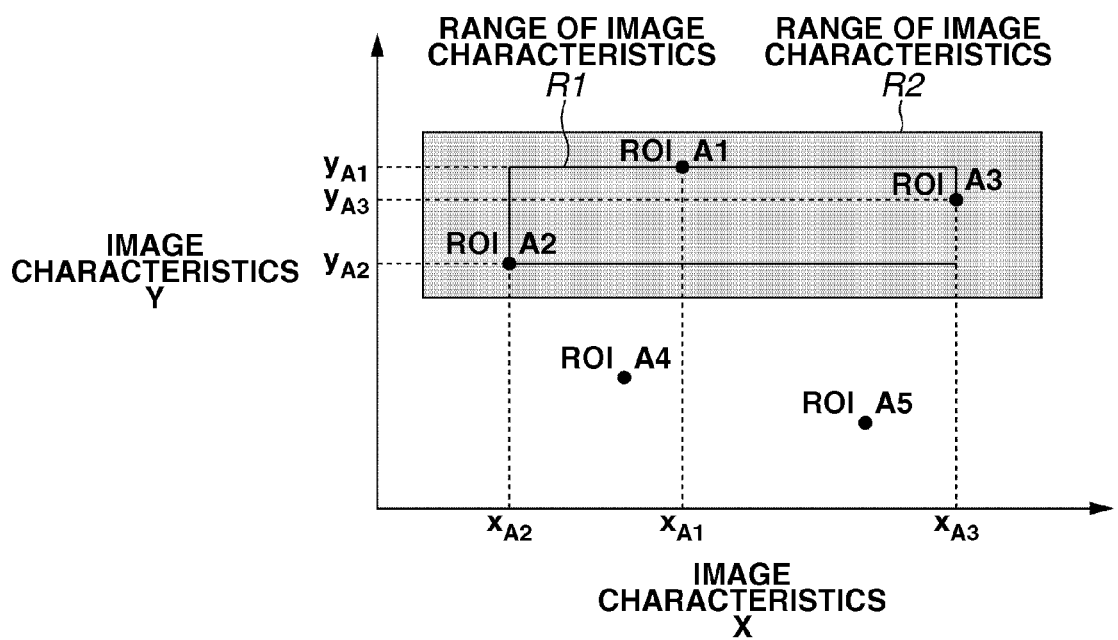
FIG. 3 is a schematic diagram illustrating the first exemplary embodiment of the present invention and exemplifying a first derivation method of image characteristic conditions to identify ROI images classified by the user as the same group.

FIG. 3 is a schematic diagram illustrating the first exemplary embodiment of the present invention and exemplifying a first derivation method of image characteristic conditions to identify ROI images as the same group, which is classified by the user.

An example having two image characteristics (X and Y) are illustrated in FIG. 3 to simplify the description, but the description below about the two image characteristics (two-dimensional space) can easily be extended to arbitrary m image characteristics (m-dimensional space, m is a natural number). It is assumed that each image characteristic is normalized and the scale between image characteristics is standardized.

Each of ROI images specified by the user to belong to the same group is positioned as a point in an m-dimensional image characteristic space in which m image characteristics have respective coordinate axes. Then, the minimum value and the maximum value are determined on each coordinate axis of coordinates of the ROI image and a range surrounded by these maximum and minimum values (m-dimensional rectangle) is defined as a range R1 of image characteristics. Further, a range R2 of image characteristics is derived by extending the range R1 of image characteristics by a predetermined margin (a predetermined value is subtracted from the minimum value and the predetermined value is added to the maximum value). Then, the presence in the range R2 of image characteristics is set as image characteristic conditions to identify any ROI image as belonging to the same group.

FIG. 3 illustrates an example in which three ROI images (ROI A1 to A3) classified into the same group are positioned at coordinates $(x_{A1}, y_{A1})$, $(x_{A2}, y_{A2})$, and $(x_{A3}, y_{A3})$ in a two-dimensional image characteristic space. Two image characteristics serve as coordinate axes in a two-dimensional image characteristic space. In the example in FIG. 3, the minimum value is $x_{A2}$ and the maximum value is $x_{A3}$ in the X-axis direction and the minimum value is $y_{A2}$ and the maximum value is $y_{A1}$ in the Y-axis direction. Based on these values, the range R1 of image characteristics illustrated in FIG. 3 is defined and further, the range R2 of image characteristics obtained by adding a margin to the range R1 of image characteristics is defined.

The margin used to extend the range R1 of image characteristics may be a fixed value regardless of the coordinate axis, but may also be a different value for each coordinate axis. For example, the value obtained by acquiring the length of each side (a difference between the maximum value and the minimum value for each coordinate axis) of the range R1 of image characteristics and dividing the length of each side by a constant may be used as a margin in the coordinate axis direction parallel to each side.

There are various kinds of image characteristics, which can roughly be divided into shape characteristics and density distribution characteristics of an abnormal shaded region. Examples of shape characteristics of the abnormal shaded region include sizes (length, area, volume), ellipticity of a boundary line, and the degree of irregularity of the boundary line. The ellipticity of a boundary line is an index indicating how elongated the abnormal shaded region is (how crushed a circle is). The ellipticity of a boundary line can be obtained by calculating an elliptic shape (called elliptic fitting) most matching the boundary line of the abnormal shaded region and then calculating the ratio of the length and the breadth of the elliptic shape. The boundary line of the abnormal shaded region can be determined by using the generally known region division method or boundary line extraction method (such as the graph cut method, watershed method, level set method, and snakes method).

The degree of irregularity is an index indicating how irregular (not smooth) the boundary line of the abnormal shaded region is. The degree of irregularity of the boundary line is obtained by calculating an amount of shift (the area of a region surrounded by two boundary lines) between the boundary line of an elliptic shape obtained by the elliptic fitting and the boundary line of the abnormal shaded region. Examples of density distribution characteristics of the abnormal shaded region include an average density value, a distribution of the density value, and a histogram of the density value.

Figure 4:
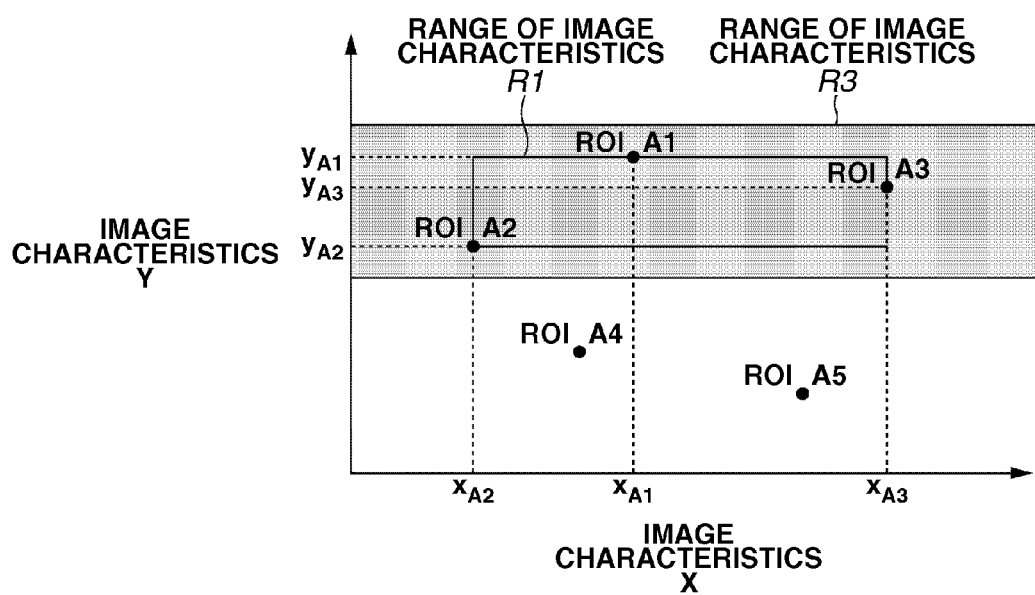
FIG. 4 is a schematic diagram illustrating the first exemplary embodiment of the present invention and exemplifying a second derivation method of image characteristic conditions to identify ROI images classified as the same group by the user as the same group.

FIG. 4 is a schematic diagram illustrating the first exemplary embodiment of the present invention and exemplifying a second derivation method of image characteristic conditions to identify ROI images as the same group, which is classified by the user.

In the second derivation method, processing up to the determination of the range R1 of image characteristics is the same as the first derivation method and a description thereof is omitted. After the range R1 of image characteristics is determined in the second derivation method, the length of each side of the range R1 is compared with a predetermined threshold and if the length of the side is equal to or less than the threshold, the range R1 of image characteristics is extended by a predetermined margin in the coordinate axis direction parallel to the side by the same method as that in FIG. 3. Conversely, if the length of the side is equal to or more than the threshold, the range R1 of image characteristics is extended indefinitely in the coordinate axis direction parallel to the side (in other words, the range is not limited). Here, a range R3 of image characteristics after the extension is derived and the presence in the range R3 of image characteristics is set as image characteristic conditions to identify any ROI image as belonging to the same group. Accordingly, image characteristics on which importance is not placed by the user can be removed from the image characteristic conditions to identify ROI images.

FIG. 4 illustrates that after the range R1 of image characteristics is defined in the same manner as in FIG. 3, the range R3 is defined by a region extended for each coordinate axis. The example in FIG. 4 exemplifies a case when the length of the side of the range R1 of image characteristics in the X-axis direction (that is, $x_{A3}-x_{A2}$) is equal to or more than the threshold and the length of the side of the range R1 of image characteristics in the Y-axis direction (that is, $y_{A1}-y_{A2}$) is equal to or more than the threshold. In this case, the range R1 of image characteristics is extended indefinitely in the X-axis direction and extended by the predetermined margin in the Y-axis direction. As a result, image characteristics X are excluded from the image characteristic conditions to identify any ROI image as belonging to the same group.

Whether to exclude each image characteristic from the conditions may be determined by other methods than the above method. For example, whether to exclude each image characteristic may be determined based on whether the dispersion of value of the image characteristic (in the example in FIG. 4, the dispersion of $x_{A1}$, $x_{A2}$, and $x_{A3}$ and the dispersion of $y_{A1}$, $y_{A2}$, and $y_{A3}$) of ROI images classified into the same group is equal to or less than a predetermined threshold. A method for excluding a predetermined number of image characteristics in descending order of length of each side of the range R1 of image characteristics or of dispersion of value, instead of comparing with a predetermined threshold, may also be used. Similarly, any other method for excluding image characteristics whose values vary among ROI images classified into the same group may be used.

FIG. 5 is a schematic diagram illustrating the report creation screen example of the report creation support apparatus according to the first exemplary embodiment of the present invention.

In FIG. 5, a graphical user interface (GUI) to input image findings common in a plurality of ROI images classified into the first group display area 221 mentioned in the description of FIG. 2 is displayed in an image findings input area 510. If n (n≥2) group display areas (not illustrated in FIG. 2) are present, an image findings input area (not illustrated) corresponding to each group is displayed.

The GUI exemplified in the image findings input area 510 is a GUI to input a plurality of image findings determined in advance, in a template format. One type of image findings is displayed in each row and values among options preliminarily determined for each type of image findings can be input (selected). In the example shown in FIG. 5, "Size", "Overall shape", "Spiculation", "Ill-defined border" and the like are displayed as the types of image findings. Examples of values of image findings for some type of image findings are illustrated below.

Values of "Size": 0.8 cm, 1.5 cm, 2.4 cm and so on
Values of "Overall shape": Spherical, round, lobate, irregular and so on
Values of "Spiculation": Many/strong, intermediate, few/weak, not recognized and so on
Values of "Ill-defined border": Many/strong, intermediate, few/weak, not recognized and so on may be selected by the user via the graphical user interface (GUI) to input image findings via the image findings input area 510. Accordingly, the graphical user interface (GUI) which serves input image findings can be considered as an input unit configured to input image findings.

As will be described below using FIGS. 6-1 and 6-2, the report creation support apparatus 1 totalizes image findings attached to a plurality of similar images obtained by performing a search of similar images. Then, the report creation support apparatus 1 extracts image findings with a high appearance ratio and displays the extracted image findings in the image findings input area as an initial value. An appropriate search for similar images can be performed only by specifying an ROI image belonging to the same group and the user can obtain as the initial value image findings from similar images, which shows a high probability of similarity. Thus, the efficiency of creating a report is efficiently increased. Further, if the user thinks that image findings input as the initial values are not appropriate, the user can manually correct any image findings and thus can take responsibility for content written in a report.

Figures 1, 6:
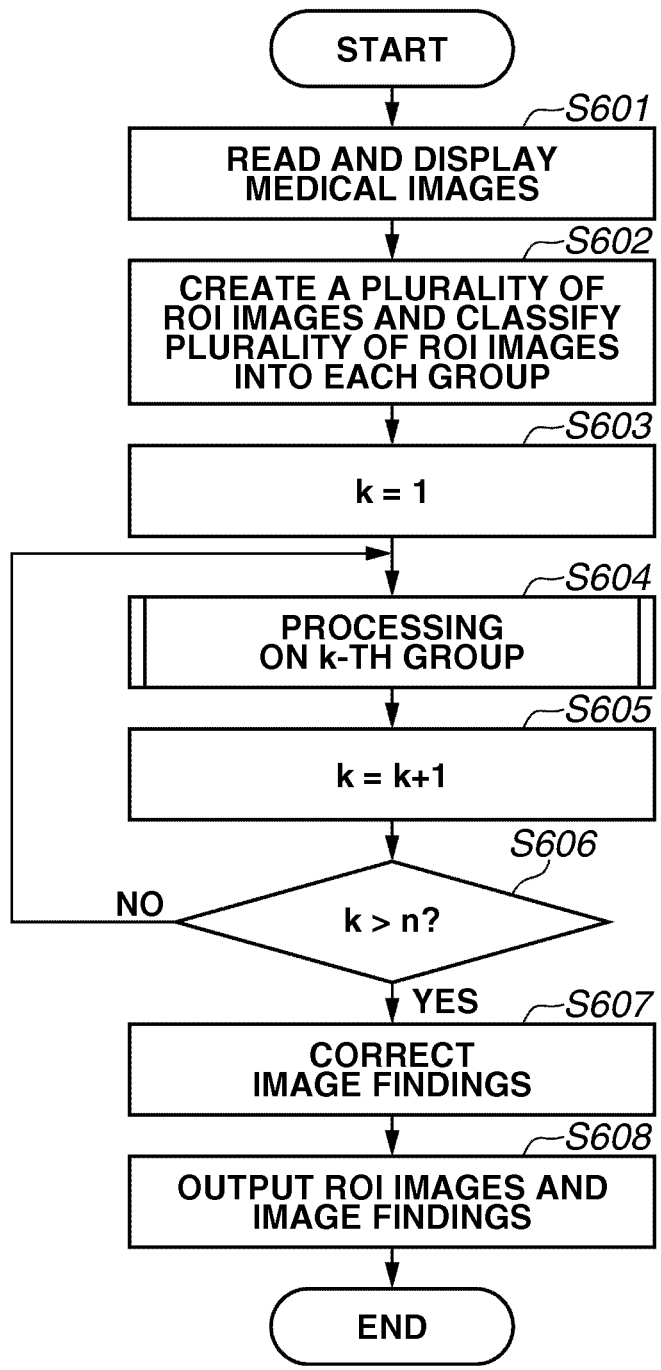
Figures 2, 6:
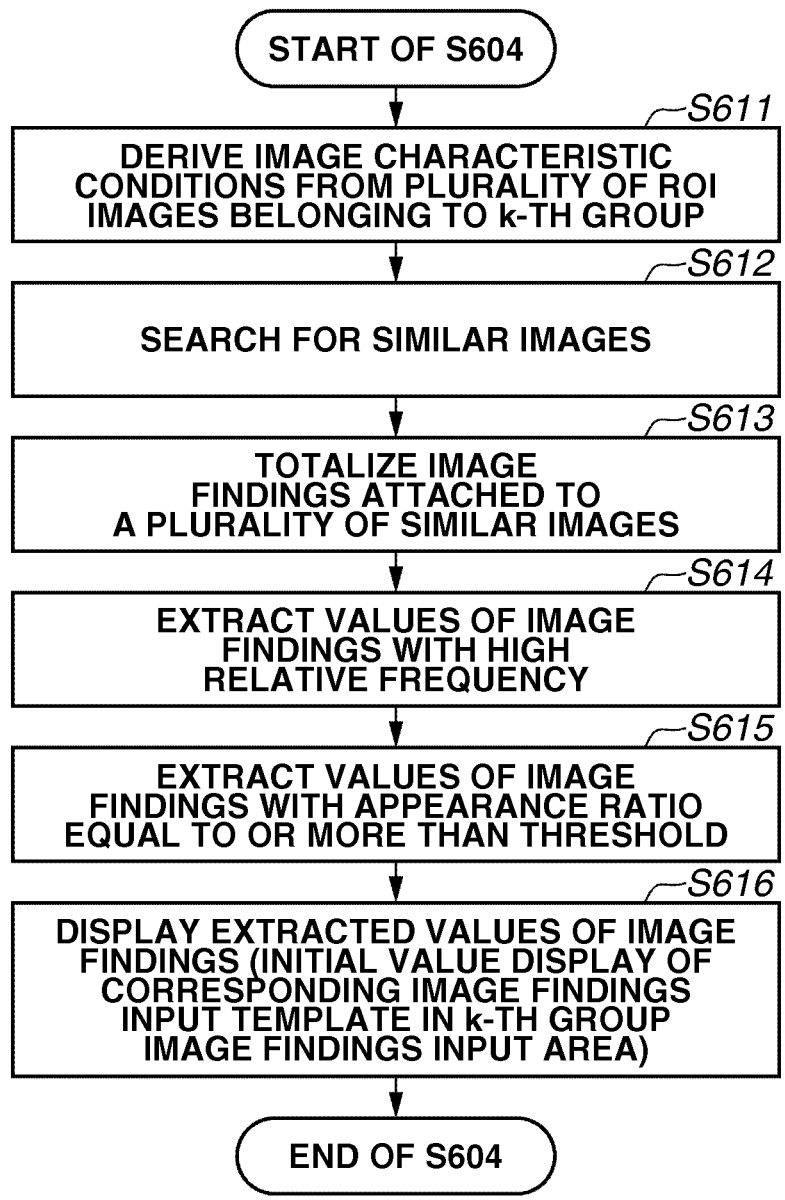

FIG. 6-1 is a flow chart exemplifying a control procedure of the report creation support apparatus according to the first exemplary embodiment of the present invention. In the example in FIG. 6-1, it is assumed that there are n groups of similar images specified by the user.

First, in step S601, the report creation support apparatus 1 reads medical image data of a patient to be diagnosed from the database 2 via the LAN 3 and temporarily stores the medical image data in the main memory 101. Then, the control unit 10 (or the CPU 100) displays a medical image in the image display area 210 of the monitor 104 by copying the medical image data to the display memory 103. If the medical image data is composed of a plurality of tomograms, the plurality of tomograms is all stored in the main memory 101. Then, any tomogram is selected according to user's instructions and the control unit 10 (or the CPU 100) displays the selected tomograms in the image display area 210 of the monitor 104 by copying the tomogram to the display memory 103.

Subsequently, in step S602, for example, the CPU 100 copies a region of interest of the medical image displayed in the image display area 210 to the main memory 101 as an ROI image according to user's instructions as described in FIG. 2. Then, the CPU 100 displays each of specified ROI images in the non-classified image group display area 222 of the monitor 104. At this point, the user can change at any time the tomogram to be displayed in the image display area 210. More specifically, the user can copy an ROI image from any position and any range of the arbitrary tomogram. In step S602, the CPU 100 further classifies the ROI image into one of the first to n-th groups of similar groups and the non-classified image group and displays the ROI image in the corresponding display area (for example, the first group display area 221) of the monitor 104. The processing proceeds from step S602 to step S603 after an instruction of "Classification completed" is issued by the user using the keyboard 106 or the mouse 105.

Subsequently, in step S603, for example, the CPU 100 initializes an index k to the value 1 for a group of similar images.

Subsequently, in step S604, for example, the CPU 100 sets ROI images of the k-th group as images to be processed and performs processing to determine and display image findings common in the ROI images in the monitor 104 as an initial value of the input template. Details of the processing in step S604 will be described in steps S611 to S616 described below (FIG. 6-2).

Subsequently, in step S605, for example, the CPU 100 increases the index k by adding the value 1 thereto.

Subsequently, in step S606, for example, the CPU 100 determines whether the value of the index k is larger than the number n of groups of similar images. If, as a result of the determination, k is equal to or less than n (No in step S606), the processing returns to step S604. On the other hand, if, as a result of the determination, k is larger than n (Yes in step S606), the processing proceeds to step S607.

After proceeding to step S607, the CPU 100 receives user's operation input to correct the initial values of image findings set in step S604 for a group of each similar image.

Subsequently, in step S608, for example, the CPU 100 outputs and stores ROI images of a group of each similar image and user-corrected image findings in the database 2 via the LAN 3. Then, the CPU 100 terminates the processing.

FIG. 6-2 is a flow chart illustrating the first exemplary embodiment of the present invention and exemplifying a detailed control procedure of step S604 in FIG. 6-1.

First, in processing in step S604 according to the present exemplary embodiment, in step S611, for example, the CPU 100 calculates predetermined image characteristics of each ROI image belonging to the k-th group by performing image processing on each ROI image. Then, the CPU 100 derives image characteristic conditions to identify a plurality of ROI images as belonging to the same group by the method described with reference to FIG. 3 or 4. Then, the CPU 100 determines an ROI image having image characteristics satisfying the image characteristic conditions, as a search condition of similar images.

Subsequently, in step S612, for example, the CPU 100 searches the database 2 (case image database) via the LAN 3 by using the search condition of similar images determined in step S611 to obtain similar images of ROI images of the k-th group. The database 2 accumulates ROI images (case images) of various cases extracted in past image diagnosis. Further, the database 2 as case images accumulates predetermined image characteristics calculated in advance and image findings attached by an image diagnostician in association with each other. It is assumed here that one or more similar images satisfying the search conditions are searched from the database.

It is assumed that, for example, r similar images ROI B1 to Br (r≥2) are obtained by the similar image search in step S612. Hereinafter, r similar images are denoted as ROI Bi (1≤i≤r). The subscript i is the index of similar images. In this case, the report creation support apparatus 1 receives r similar images ROI Bi (1≤i≤r) and image findings Fi1 to Fiq$_i$ (1≤i≤r, q$_i$≥2) from the database 2. The subscript q$_i$ is the number of image findings attached to the similar image ROI Bi and is a different value for each similar ROI image (for each index i).

Subsequently, for example, the CPU 100 performs processing to extract an image findings satisfying predetermined conditions from among image findings obtained in step S612. In the present exemplary embodiment, image findings with a high appearance ratio is extracted by processing in steps S613, S614, and S615 shown below. First, in step S613, for example, the CPU 100 totalizes the appearance frequency for each value of image findings based on image findings Fi1 to Fiq$_i$ (1≤i≤r, q$_i$≥2) obtained in step S612. Accordingly, for example, the CPU 100 calculates the ratio (appearance ratio) of each value of image findings attached to similar images. In the example in FIG. 5, for example, for the type of image findings of "Overall shape", the CPU 100 calculates the appearance ratio of each value of "Overall shape:spherical", "Overall shape:round", "Overall shape:lobate", and "Overall shape:irregular".

Subsequently, in step S614, for example, the CPU 100 extracts the value of image findings with a high appearance ratio by referring to calculation results of the appearance ratio obtained in step S613. More specifically, the CPU 100 compares the appearance ratios of values of image findings for each type of image findings to extract the value of the highest appearance ratio. For the type of image findings of, for example, "Overall shape", it is assumed that the appearance ratio of "Overall shape:spherical"=0.3, the appearance ratio of "Overall shape:round"=0.5, the appearance ratio of "Overall shape:lobate"=0.1, and the appearance ratio of "Overall shape:irregular"=0.1. In this case, the value of "Overall shape:round" is extracted as the value of image findings with the highest appearance ratio in the type of image findings of "Overall shape". If two or more values of image findings (for example, "spherical" and "round") with the highest appearance ratio are present in some type of observations (for example, "Overall shape"), for example, the value extracted first is selected here to select one value.

Subsequently, in step S615, for example, the CPU 100 compares the appearance ratio of the value of image findings extracted in step S614 with a predetermined threshold to extract only the value of image findings having an appearance ratio equal to or more than the threshold. If, for example, the threshold of the appearance ratio is 0.3, the appearance ratio of "Overall shape:round" extracted in step S614 is 0.5 and larger than the threshold (0.3) and thus, "Overall shape:round" is also selected in the present step.

The value of image findings with the highest appearance ratio and having an appearance ratio equal to or larger than the threshold can be extracted for each type of image findings in the steps S614 and S615. However, no value of image findings having an appearance ratio equal to or larger than the threshold may be present depending on the type of image findings and no value is extracted for such image findings.

Subsequently, in step S616, for example, the CPU 100 displays (inputs into a report) the value of image findings extracted in the steps S614 and S615 as the initial value of a corresponding image findings input template in the image findings input area for the k-th group. In the example in FIG. 5, values of image findings of "Round", "Not recognized", and "Many/strong" are extracted and displayed as the initial values for the three types of image findings of "Overall shape", "Spiculation", and "Ill-defined border". On the other hand, no initial value is displayed for the other types of image findings because no value of image findings having an appearance ratio equal to or larger than the threshold is extracted.

The processing in step S604 in FIG. 6-1 according to the present exemplary embodiment is realized by undergoing the above steps S611 to S616.

The second exemplary embodiment of the present invention will be described below using FIGS. 7 to 11 with reference to FIGS. 2 and 6. However, an apparatus configuration example of the report creation support apparatus according to the second exemplary embodiment is also illustrated by FIG. 1 similar to the first exemplary embodiment and thus, the description of the apparatus configuration example is omitted.

Figure 7:
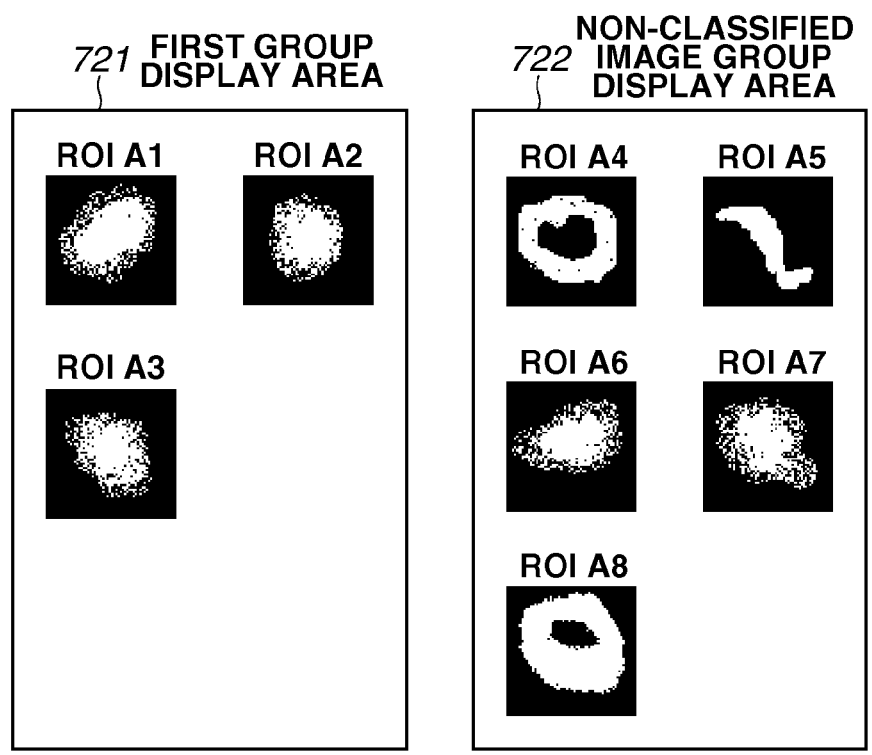
FIG. 7 is a diagram illustrating a first image display screen example of the report creation support apparatus according to a second exemplary embodiment of the present invention.

FIG. 7 is a diagram illustrating a first image display screen example of the report creation support apparatus according to the second exemplary embodiment of the present invention. A display area similar to that in FIG. 2 is displayed in FIG. 7. However, the image display area 210 illustrated in FIG. 2 is omitted.

In FIG. 7, like in FIG. 2, similar ROI images (ROI A1 to A3) classified at the user's choice are displayed in the first group display area 721. In addition, non-classified ROI images (ROI A4 to A8) are displayed in the non-classified image group display area 722.

Figure 8:
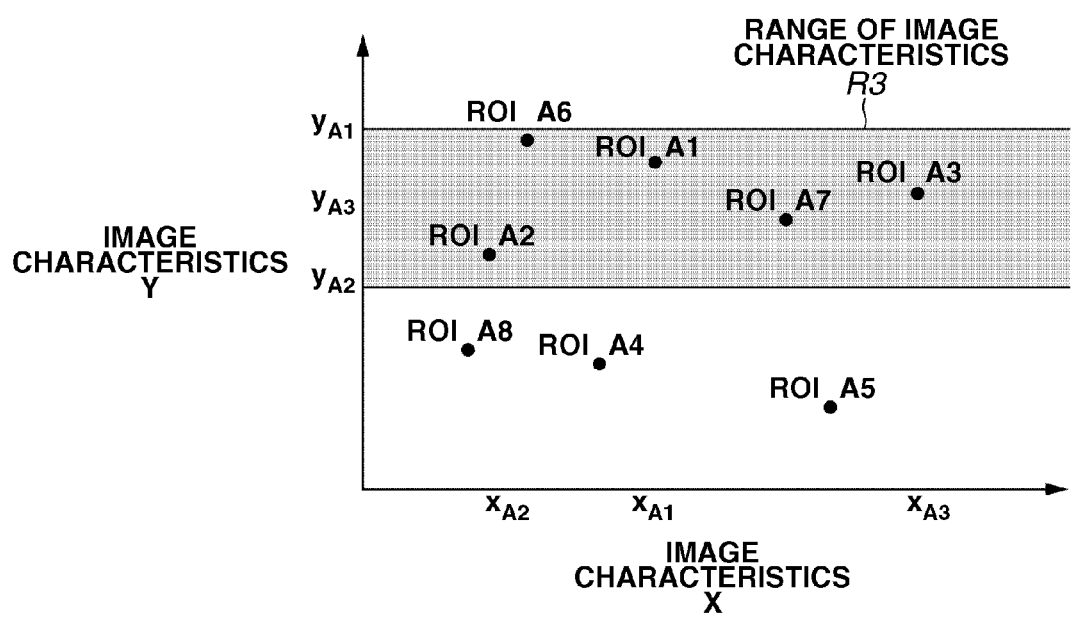
FIG. 8 is a schematic diagram illustrating the second exemplary embodiment of the present invention and exemplifying a distribution of ROI images exemplified in FIG. 7 in an image characteristic space exemplified in FIG. 4.

FIG. 8 is a schematic diagram illustrating the second exemplary embodiment of the present invention and exemplifying a distribution of ROI images exemplified in FIG. 7 in an image characteristic space exemplified in FIG. 4.

If image characteristic conditions to identify the first group are derived by the second derivation method in the first exemplary embodiment, the range R3 of image characteristics like in the first exemplary embodiment can be obtained. It is assumed here that ROI A6 and A7 of non-classified ROI images exemplified in FIG. 7 are distributed in the range of the range R3 of image characteristics. In such a case, though not yet classified by the user, processing is performed to determine that ROI A6 and A7 are ROI images that should be classified into the first group and to automatically classify these non-classified ROI images into the first group.

Figure 9:
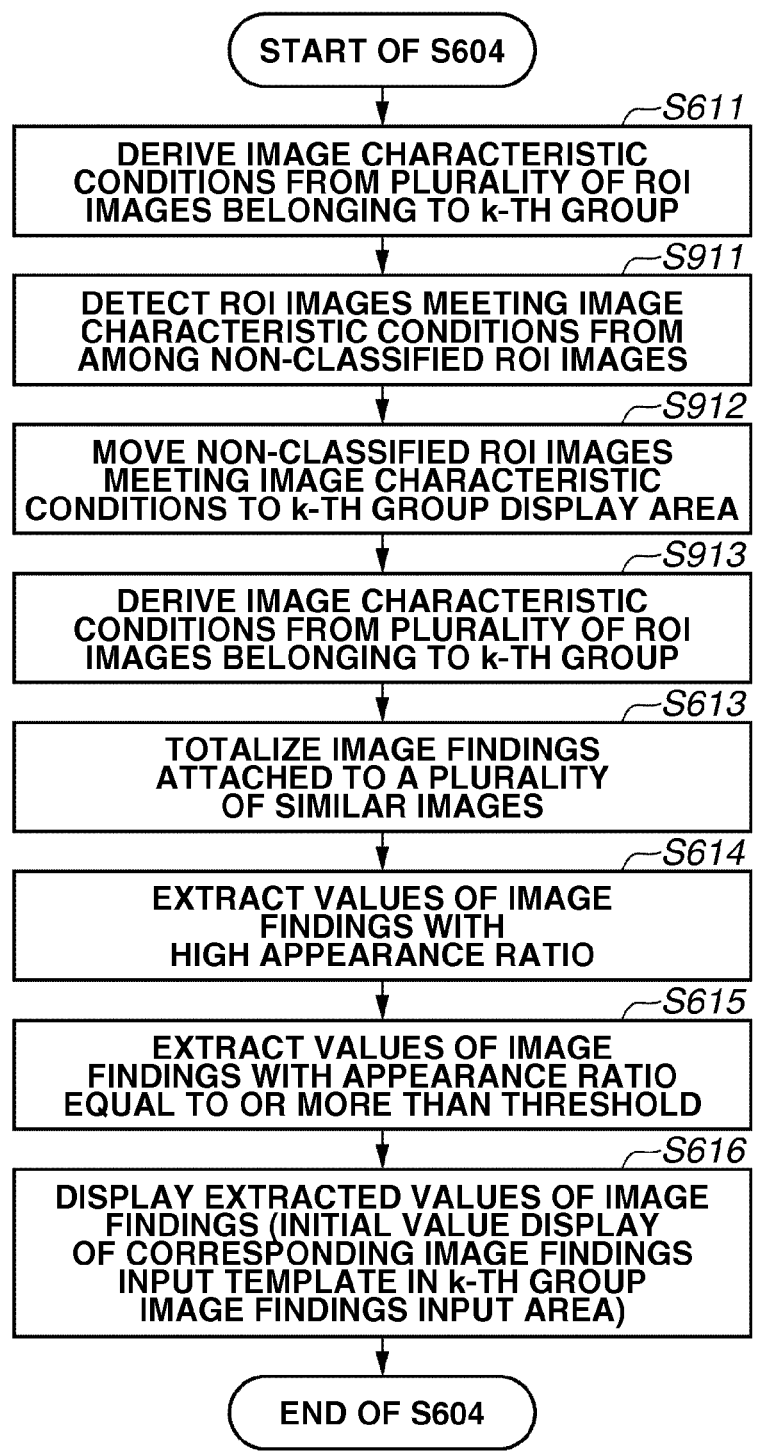
FIG. 9 is a flow chart illustrating the second exemplary embodiment of the present invention and exemplifying the detailed control procedure of step S604 in FIG. 6-1.

FIG. 9 is a flow chart illustrating the second exemplary embodiment of the present invention and exemplifying the detailed control procedure of step S604 in FIG. 6-1.

FIG. 9 illustrates a portion of the control procedure for automatically classifying non-classified ROI images satisfying conditions of the k-th group into the k-th group. FIG. 9 omits the steps S601 to S607 illustrated in FIG. 6-1. The non-illustrated steps S601 to step S607, step S611, and steps S613 to S616 are the same as the control procedure described in the first exemplary embodiment and thus, the description thereof is omitted.

The control procedure in FIG. 9 is different from the control procedure described in FIG. 6-2 in that steps S911 to S913 are added between step S611 and step S613 in FIG. 6-2.

First, in processing in step S604 according to the present exemplary embodiment, in step S611, for example, the CPU 100 calculates predetermined image characteristics of each ROI image belonging to the k-th group by performing image processing on each ROI image. Then, the CPU 100 derives image characteristic conditions to identify a plurality of ROI images as belonging to the same group by the method described with reference to FIG. 3 or 4.

Subsequently, in step S911, for example, the CPU 100 calculates predetermined image characteristics of each non-classified ROI image displayed in the non-classified image group display area by performing image processing on each ROI image. Then, for example, the CPU 100 detects ROI images satisfying the image characteristic conditions derived in step S611 as ROI images to be added to the k-th group. In the example in FIGS. 7 and 8, ROI A6 and A7 are detected.

Subsequently, in step S912, for example, the CPU 100 moves the non-classified ROI images detected in step S911 from the non-classified image group display area to the k-th group display area. In the example in FIG. 7, ROI A6 and A7 are moved from a non-classified image group display area 722 to a first group display area 721.

Subsequently, in step S913, for example, the CPU 100 derives image characteristic conditions again from a plurality of ROI images belonging to the k-th group by performing processing similar to that in step 611. The image characteristic conditions are derived again in the present step to take an influence of addition of the ROI images belonging to the k-th group in step S912 into consideration. This influence will be described using FIGS. 8 and 10.

Figure 10:
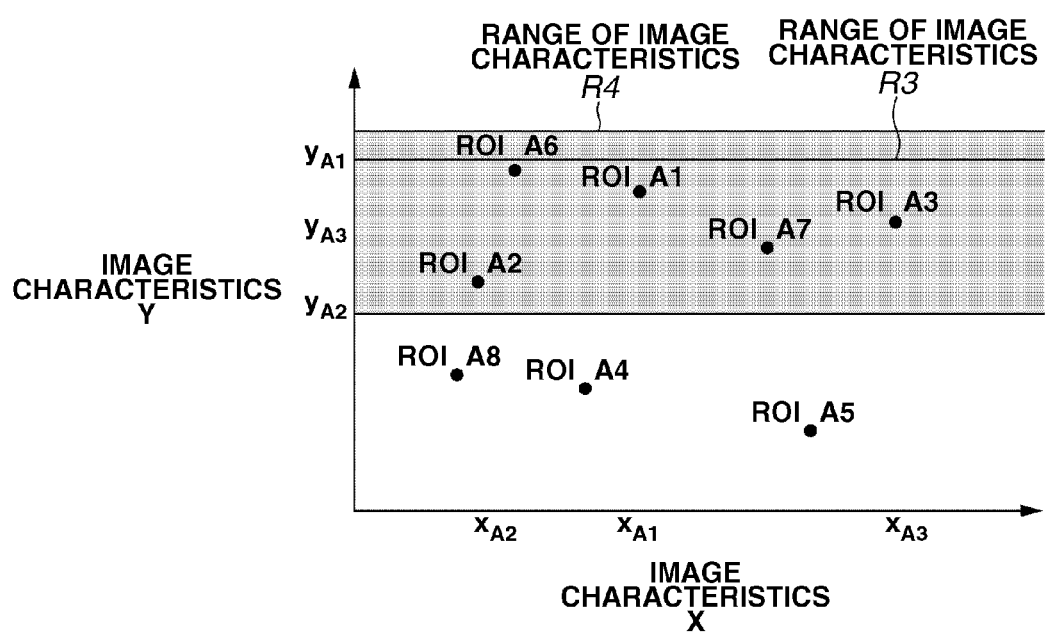
FIG. 10 is a schematic diagram illustrating the second exemplary embodiment of the present invention and exemplifying extension of a range R3 of image characteristics exemplified in FIG. 8 to a range R4 of image characteristics.

FIG. 10 is a schematic diagram illustrating the second exemplary embodiment of the present invention and exemplifying extension of the range R3 of image characteristics exemplified in FIG. 8 to a range R4 of image characteristics. In FIG. 8, if, for example, ROI A6 is distributed near the boundary inside the range R3 of image characteristics, the range R3 of image characteristics is extended by a predetermined margin from ROI A6 by the processing in step S913 to obtain the range R4 of image characteristics. Then, new image characteristic conditions are specified by the range R4 of image characteristics.

Figure 11:
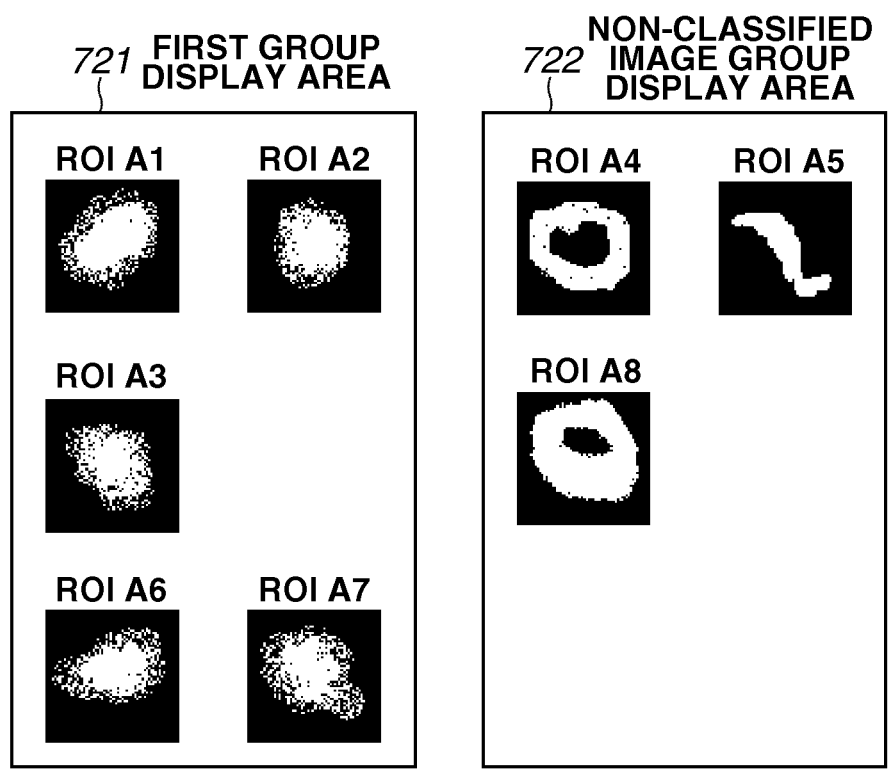
FIG. 11 is a diagram illustrating a second image display screen example of the report creation support apparatus according to the second exemplary embodiment of the present invention.

FIG. 11 is a diagram illustrating a second image display screen example of the report creation support apparatus according to the second exemplary embodiment of the present invention. The result illustrated in FIG. 10 is obtained by the control procedure described with reference to FIG. 9. More specifically, in addition to ROI images ROI A1 to A3 classified by the user, ROI images ROI A6 and A7 that are not classified, but are similar in image characteristics are automatically classified into the first group display area 721. Accordingly, if the user classifies some similar ROI images, remaining similar ROI images are automatically classified so that classification work of ROI images can also be made more efficient.

Then, in FIG. 9, the processing in step S604 in FIG. 6-1 according to the present exemplary embodiment is realized by undergoing steps S613 to S616 in FIG. 6-2.

According to the report creation support apparatus 1 in the present invention, as described above, a similar image search is performed by using image characteristic conditions common to an plurality of diagnosis target images selected by the user and therefore, a similar image search fitting for the user's choice is carried out. Further, an image findings with a high probability can be written in a report by extracting image findings attached with a high frequency to one or more similar images obtained by the similar image search.

Other Embodiments

The present invention can be realized by performing the following processing. Software (program) is supplied to the system or the apparatus via a network or various storage media and a computer (or a CPU or MPU) of a system or an apparatus performs the processing by reading software (program) realizing functions of the above exemplary embodiments. The program and a computer readable recording medium storing the program are included in the present invention.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2010-264922 filed Nov. 29, 2010, which is hereby incorporated by reference herein in its entirety.

What is claimed is:

1. An apparatus for obtaining images similar to a diagnosis target image, comprising:
   a selector configured to select medical images specified by a user, the selected medical images each including image data representing a region of interest selected from within the diagnosis target image;
   a receiver configured to obtain, based on each of the selected medical images, an evaluation, from the image data representing the region of interest within each of the selected medical images, of an evaluation item common to the selected medical images;
   a determiner configured to determine a range based on each of the obtained evaluations, the range defining a space including evaluation values for indicating whether other medical images are similar to the selected medical images; and
   a central processing unit configured to search a database for one or more other medical images based on the determined range.

2. The apparatus according to claim 1, wherein the receiver is configured to derive image characteristics, as the evaluation, from each of the selected medical images, the derived image characteristics defining the range of similarity; and
   the apparatus further comprises:
   an extractor configured to extract an image observation parameter satisfying predetermined conditions from image observation parameters attached to the one or more similar images obtained by the central processing unit; and
   a provider configured to input image findings extracted by the extractor into the report as image findings common to the selected medical images.

3. The apparatus according to claim 1, wherein the receiver is configured to derive image characteristics from each of the selected medical images, the derived image characteristics defining the range of similarity; and
   the apparatus further comprises:
   a detector configured to detect medical images satisfying the image characteristic conditions derived by the receiver from among the selected medical images for which no group is specified by the user.

4. The apparatus according to claim 1, wherein
   the receiver is configured to perform a process, corresponding to the evaluation item, on each of the selected medical images to obtain a value of an image characteristic as the evaluation.

5. The apparatus according to claim 1, wherein
   the central processing unit is configured to search a database for one or more medical images included in the determined range.

6. The apparatus according to claim 1, wherein
   the central processing unit is configured to search the database including medical images each associated with image findings therefor, confirmed by a medical doctor, the apparatus further comprises:
an extractor configured to extract an image finding based on the medical images found by the central processing unit.

7. The apparatus according to claim 6, further comprising:
a controller configured to cause a monitor to display the extracted image finding as a proposal for an input for a medical diagnosis report of the diagnosis target image.

8. The apparatus according to claim 7, further comprising:
another receiver configured to receive information of an operation, on an operation unit, by a user, for confirming and modifying the extracted and displayed image finding for an input of the medical diagnosis report; and
a transmitter configured to output the diagnosis report including the confirmed image finding.

9. The apparatus according to claim 6, further comprising:
a controller configured to cause a monitor to display a list of categories of the image findings for the diagnosis target image and areas for inputting image findings for the categories,
wherein the controller is configured to display the extracted image finding in an area of the displayed areas corresponding to a category of the extracted image finding.

10. The apparatus according to claim 1, further comprising:
a categorizer configured to categorize, according to an operation of the user, the selected medical images into groups, each of the groups corresponding to one of target medical images,
wherein the determiner is configured to determine, for each of the groups, a range based on each of the obtained evaluation for one of the categorized medical images.

11. The apparatus according to claim 1, wherein
the selector is configured to select medical images from a plurality of diagnosis target images.

12. The apparatus according to claim 1, wherein
the receiver is configured to obtain, based on each of the selected medical images and the diagnosis target image, an evaluation of the evaluation item common to the selected medical images and the diagnosis target image.

13. A method for obtaining images similar to a diagnosis target image, comprising:
selecting medical images specified by a user, the selected medical images each including image data representing a region of interest selected from within the diagnosis target image;
obtaining, based on each of the selected medical images, an evaluation, from the image data representing the region of interest within each of the selected medical images, of an evaluation item common to the selected medical images;
determining, based on each of the obtained evaluations, a range defining a space including evaluation values for indicating whether other medical images are similar to the selected medical images; and
searching a database for one or more other medical images based on the determined range.

14. A non-transitory computer-readable storage medium storing thereon a computer-executable program to cause a computer to the method of claim 13.

15. An apparatus for outputting a medical diagnosis report of a diagnosis target image, the apparatus comprising:
a selector configured to select medical images specified by a user, the selected medical images each including image data representing a region of interest selected from within the diagnosis target image;
a central processing unit configured to search a database for other medical images based on information included in the selected images, the information including values for indicating whether other medical images are similar to the selected medical images;
an extractor configured to extract an image finding based on the other medical images found by the central processing unit;
a controller configured to cause a monitor to display:
a list of categories of the image findings for the diagnosis target image;
areas for inputting image findings for the categories; and
the extracted image finding in an area of the displayed areas corresponding to a category of the extracted image finding;
a receiver configured to receive information of an operation on an operation unit, by a user, for confirming and modifying the extracted and displayed image finding for an input of the medical diagnosis report; and
a transmitter configured to output the diagnosis report including the confirmed image finding.

16. A system including apparatuses, for obtaining images similar to a diagnosis target image, comprising:
a selector configured to select medical images specified by a user, the selected medical images each including image data representing a region of interest selected from within the diagnosis target image;
a receiver configured to obtain, based on each of the selected medical images, an evaluation, from the image data representing the region of interest within each of the selected medical images, of an evaluation item common to the selected medical images;
a determiner configured to determine a range based on each of the obtained evaluations, the range defining a space including evaluation values for indicating whether other medical images are similar to the selected medical images; and
a central processing unit configured to search a database for one or more other medical images based on the determined range.

17. A system including apparatuses, for outputting a medical diagnosis report of a diagnosis target image, the system comprising:
a selector configured to select medical images specified by a user, the selected medical images each including image data representing a region of interest selected from within the diagnosis target image;
a central processing unit configured to search a database for other medical images based on information included in the selected images, the information including values for indicating whether other medical images are similar to the selected medical images;
an extractor configured to extract an image finding based on the other medical images found by the central processing unit;
a controller unit configured to cause a monitor to display:
a list of categories of the image findings for the diagnosis target image;
areas for inputting image findings for the categories; and
the extracted image finding in an area of the displayed areas corresponding to a category of the extracted image finding;
a receiver configured to receive information of an operation on an operation unit, by a user, for confirming and modifying the extracted and displayed image finding for an input of the medical diagnosis report; and a transmitter configured to output the diagnosis report including the confirmed image finding.

18. A method for outputting a medical diagnosis report of an diagnosis target image, the method comprising:

selecting medical images specified by a user, the selected medical images each including image data representing a region of interest selected from within the diagnosis target image;

searching a database for other medical images based on information included in the selected images;

extracting an image finding based on the other medical images found by the central processing unit, the information including values for indicating whether other medical images are similar to the selected medical images;

causing a display unit to display:
- a list of categories of the image findings for the diagnosis target image;
- areas for inputting image findings for the categories; and
- the extracted image finding in an area of the displayed areas corresponding to a category of the extracted image finding;

receiving information of an operation on an operation unit, by a user, for confirming and modifying the extracted and displayed image finding for an input of the medical diagnosis report; and outputting the diagnosis report including the confirmed image finding.

19. A non-transitory computer-readable storage medium storing thereon a computer-executable program to cause a computer to execute the method of claim 18.

\* \* \* \* \*